US005718900A

United States Patent [19]

Hill et al.

[11] Patent Number: 5,718,900

[45] Date of Patent: Feb. 17, 1998

[54] VACCINES AND METHODS FOR PREVENTING AND TREATING *FESCUE TOXICOSIS* IN HERBIVORES

[75] Inventors: Nicholas S. Hill; Frederick N. Thompson, Jr.; John A. Stuedemann, all of Athens; Donald L. Dawe, High Shoals, all of Ga.

[73] Assignee: University of Georgia Research Foundation, Inc., Athens, Ga.

[21] Appl. No.: 326,734

[22] Filed: Oct. 20, 1994

Related U.S. Application Data

[63] Continuation of Ser. No. 7,141, Jan. 21, 1993, abandoned.

[51] Int. Cl.[6] .......... A61K 39/385

[52] U.S. Cl. .......... 424/194.1; 424/193.1; 514/885; 530/403; 530/807

[58] Field of Search .......... 530/363, 367, 530/409, 403, 404, 405, 807; 424/193.1, 194.1, 450, 457, 489; 435/961; 436/543, 815, 822; 514/885, 964

[56] References Cited

U.S. PATENT DOCUMENTS

| | | | |
|---|---|---|---|
| 3,224,945 | 12/1965 | Tyler, Jr. | 435/119 |
| 4,591,552 | 5/1986 | Neurath | 435/7 |
| 4,755,519 | 7/1988 | Dougherty et al. | 514/276 |
| 5,468,486 | 11/1995 | Reddick et al. | 424/194.1 |

OTHER PUBLICATIONS

Shelby & Kelley, "An Immunoassay for Ergotamine and Related Alkoids" *J. Agric. Food Chem.*, 38:1130–1134 (1990).

Shelby & Kelley, "Detection of Ergot Alkaloids from *Claviceps* Species in Agricultural Products by Competitive ELISA Using a Monoclonal Antibody" *J. Agric. Food Chem.* 40:1090–1092 (1992).

Aguado, M. T. et al., "Controlled–Release Vaccines–Biodegradable Polylactide/Polyglycolide (PL/PG) Microspheres as Antigen Vehicles," *Immunobiol.* 184:113–125 (1992).

Putnam, M. R. et al., "Effects of the Fungal Endophyte *Acremonium coenophialum* in Fescue on Pregnant Mares and Foal Viability," *Am. J. Vet. Res.*, 52(12):2071–2074 (Dec. 1991).

Testereci, H. et al., "*Fescue toxicosis:* Cattle Response to IV Infusion of an Ergovaline Enriched Fraction in a Climate Controlled Chamber," In *Proc. Amer. Foliage and Grassland Conference*, Columbia, Missouri (Apr. 1–4, 1991).

(List continued on next page.)

*Primary Examiner*—Ponnathapura Achutamurthy
*Attorney, Agent, or Firm*—Needle & Rosenberg, P.C.

[57] ABSTRACT

An immunogenic compound comprising the formula:

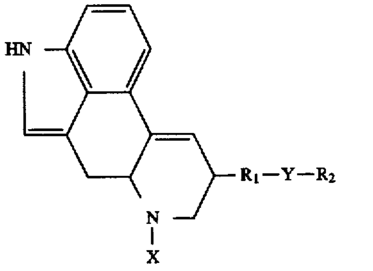

wherein X is selected from the group consisting of methyl and hydrogen;
wherein $R_1$ is a suitable functional group of the lysergic ring;
wherein $R_2$ is an immunogenic protein; and
wherein Y is a bridge to link $R_1$ to $R_2$.

Purified polyclonal and monoclonal antibodies specifically reactive with the immunogenic compound and reactive with the lysergic ring of ergopeptine and clavine alkaloids are described. An antibody which is an anti-idiotype of the monoclonal antibody is provided. Methods of prevention and treatment of fescue toxicosis utilizing the immunogenic compounds and antibodies of the present invention are provided.

18 Claims, 2 Drawing Sheets

OTHER PUBLICATIONS

Chanh, T. C. et al., "Contemporary Issues in toxicology Anti-idiotype-based Vaccines against Biological Toxins," *Toxicology and Applied Pharmacology,* 108:183–193 (1991).

Dougherty, C. T. et al., "Induction of Tall Tescue Toxicosis in Heat-Stressed Cattle and its Alleviation with Thiamin[1,2]" *J. Anim. Sci.,* 69:1008–1018 (1991).

Mizinga, K. M., "The Effect of Feeding Endophyte-Infected Fescue Seed on Luteinizing Hormone Secretion in Cows and Neural Dopamine Receptors in Rats," *Ph.D. Dissertation* University of Georgia, Athens, Georgia (1991) pp. 1–10.

Savary, B. J. et al., "Analysis of Ergopeptine Alkaloids in Bovine Iserum," *Int. Symposium on Acremonium/Grass Interactions* 263. (Abstr.) Louisiana State University, New Orleans, Louisiana (1990).

Robbins, R. J., "The Measurement of Low-Molecular-Weight, Non-Immunogenic Compounds of Immunoassay," *Immunology in Plant Sciences,* Springer-Verlag, New York (1986) pp. 86–141.

Cohen, Basic & Clinical Immunology, Fudenberg et al. (Ed.), Lange Medical Publications, Los Altos, California, pp. 596–605 (1976).

Goodman, Basic & Clinical Immunology, Fudenberg et al. (Ed.), Lange Medical Publications, Los Altos, California, pp. 32–40 (1976).

Robins et al., Immunoassays in Food Analysis, Morris et al. (Eds). Elsevier Applied Science, London, pp. 197–211 (1985).

Shelby et al., Food & Agricultural Immunology, vol. 3, pp. 169–177 (1991).

Ruitt et al., Immunology, 3rd Edition, Mosby, St. Louis, pp. 16.1–16.22 (1993).

Arens et al (1980) Planta Med 39(4):336–47.

Taunton-Rigby et al (1973) Science 181 (4095):165–6.

Loeffler et al (1973) J. Pharm. Sci 62(11):1817–20.

Voss et al (1972) Psychopharmacologia 26(2):140–5.

Ratcliffe et al (1977) Clin. Chem. (Winston-Salem, N.C.) 23(2 Pt 1) 169–74.

Vurakis et al (1971) Proc. Natl. Acad. Sci USA 68:1483–87.

Riddick, et al., "Development of an Immunoassay for Detection of Ergoline Alkaloids in Tall Fescue" *Tenn. Farm Home Sci.,* 160,78–81 (1991).

DE-A-40 31 283 (Kwizda Fa F Johann) 2 May 1991.

Derwent Publications, Ltd. London, 68; Class B04, AN 81-244290 XP002023900 & [JP-A-56 014 948 (Teikoku Hormone Mfg Ltd), 13 Feb. 1981] "Immunochemical Lysergic Acid Derivative Analyse and Quantity Radioactive Label Lysergic Acid Antibody Measure Radioactive Free Combination Lysergic Acid" Database WPI Section Ch, Week 8114.

Goding, James W., "Antibody Production by Hybridomas" *Jornal of Immunological Methods,* 39:285–308 (1980).

Kieber-Emmons, et al., "Rational Design and Application of Idiotope Vaccines" *International Reviews of Immunology,* 1:1–26(1986).

VACCINES AND METHODS FOR PREVENTING AND TREATING *FESCUE TOXICOSIS* IN HERBIVORES

This application is a continuation of application Ser. No. 08/007,141, filed Jan. 21, 1993, abandoned.

This invention was made with government support under College of Veterinary Medicine Experiment Station Funds and College of Agriculture Experiment Station Funds. This invention was also made with government support under CRIS Project No. 6613-31630-001-00 D awarded by USDA, ARS. The government has certain rights in the invention.

BACKGROUND OF THE INVENTION

1. Field of the Invention

This invention relates to vaccines useful to prevent and treat fescue toxicosis in herbivores. More particularly, this invention provides immunogenic compounds, a hybridoma cell line which produces monoclonal antibodies and an anti-idiotype vaccine to prevent and treat fescue toxicosis.

2. Background Art

Fescue toxicosis is a condition of livestock associated with grazing tall fescue (*Festuca arundinacea* Schreb) infected with its fungal endophyte *Acremonium coenophialum* Morgan-Jones and Gams. Inasmuch as tall fescue is widely adapted and utilized (Burns and Chamblee, 1979) and incidence of endophyte infection within pastures is high (Hill and Stringer, 1985; Shelby and Dalrymple, 1987), fescue toxicosis is a widespread problem and represents a major economic loss to the livestock industry in the United States.

Tall fescue plantings occupy over 35 million acres in the United States and Canada wherein over 90% of this acreage is infected with *Acremonium coenophialum (Bacon et at.,* 1988). Extreme expense and environmental concerns make it impractical, if not impossible to approach the problem of fescue toxicosis by replanting affected acreage with endophyte-free cultivars. Moreover, the endophyte and plant appear to exist in a symbiotic relationship, suggesting potential problems with the long term survival of endophyte-free cultivars.

Signs of fescue toxicosis include lethargy, reduced weight gain, increased respiration, gangrenous lesions on the extremities, and roughened hair coats. Physiologically, affected livestock have reduced serum cholesterol and alkaline phosphatase (Bond et al., 1984; Stuedemann et al., 1985; Lipham et al., 1989), decreased visceral and peripheral blood flow (Garner et al., 1978), increased D2 receptor affinity in the corpus striatum (Mizinga, 1991), and reduced prolactin secretion (Lipham et al., 1989). Therefore the pathophysiology of fescue toxicosis includes effects on basal metabolism, cardiovascular, central nervous, and endocrine systems.

The toxic compounds of *Acremonium coenophialum* infected fescue have yet to be conclusively identified (Putnam et al., 1991). Four classes of alkaloids produced by the endophyte/tall fescue association (loline, peramine, clavine, and ergopeptine) are potentially toxic to grazing livestock. The endophyte a clavicepitaceous organism, produces ergopeptine alkaloids. Ergopeptine alkaloids are lysergic acid derivatives including agroclavine, elymoclavine, ergovaline, ergosine, and ergocornine (Siegel et al., 1991). In addition, plant derived loline alkaloids are produced in response to the fungal endophyte which are presumed to have a regulatory role in limiting endophyte habitat within the plant. These loline alkaloids are also suspected of being involved with the toxicosis syndrome (Bush et al., 1979). The loline alkaloids include the pyrrolizidine bases N-formyl loline, N-acetyl loline, and loline alkaloids (pyrrolizidine alkaloids).

Many attempts have been made to identify the alkaloid components of endophyte infected tall fescue which produce fescue toxicosis without a definitive answer. Although the unsaturated pyrrolizidine alkaloids have hepatotoxic activity (Mattocks, 1971) intraruminal infusion of saturated pyrrolizidine alkaloids found in tall fescue produced no symptoms of fescue toxicosis (Yates, 1973). However, in combination with acetylcholine, saturated pyrollizidine alkaloids are endowed with smooth muscle contracting capabilities which could result in gangrenous conditions (Bruce et al., 1971).

University of Kentucky researchers reported pyrrolizidine alkaloids as the major toxin associated with fescue toxicosis and demonstrated that thiamine treatment partially alleviated symptoms associated with the disease (Doughtery et al., 1991) (See also U.S. Pat. No. 4,755,519).

However, another group has previously shown that dorsal pedal veins contracted in vitro when exposed to various concentrations of purified lysergic acid derivatives but a mixture of pyrrolizidine alkaloids failed to produce contractile responses (Solomons et al., 1989).

Circumstantial evidence exists that the ergopeptine alkaloids are responsible for fescue toxicosis (Testereci et al., 1991). It has been shown that serum prolactin is frequently decreased in cattle grazing endophyte-infected tall fescue (Thompson et al., 1987) and ergot alkaloids are potent inhibitors of prolactin secretion (Goldstein et al., 1980). In addition, administration of metoclopramide, a type D2 receptor antagonist, increased serum prolactin and weight gains, and changed hair coats from classical fescue toxicosis appearances of long, rough and bronzed to black and shiny in Angus steers (Lipham a al., 1989). Metoclopramide, however, has minor cross reactivity with other receptors which does not exclude effects other than type D2 activity. Likewise, in vitro research evaluating the vasoconstrictive effects of alkaloids assumes that ingestion of tall fescue results in their presence in serum (Solomons et al., 1989).

Therefore, as can be appreciated by a review of the literature, the cause of fescue toxicosis remains unresolved. In addition, despite great economic losses, no economically feasible method to prevent or treat fescue toxicosis exists.

The present invention satisfies this long felt need to protect livestock from fescue toxicosis by providing antibodies and compounds for immunization against fescue toxicosis as well as a method of therapy for affected animals.

SUMMARY OF THE INVENTION

Figure 1A:
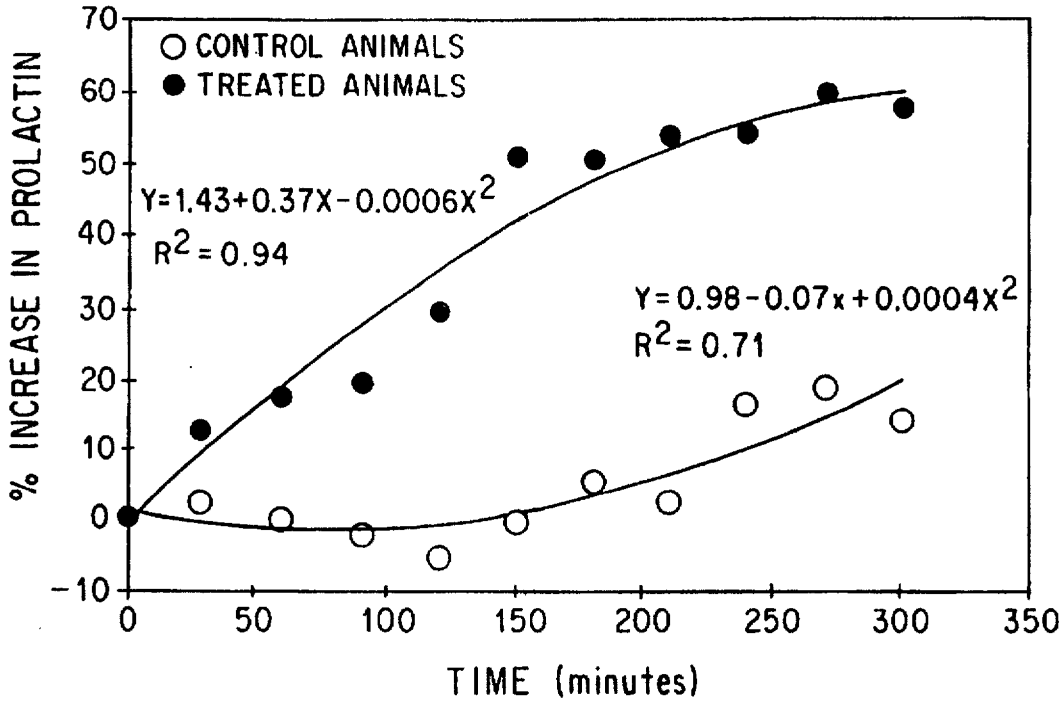
FIG. 1*a* depicts percentage changes in serum prolactin from three basal values collected at 30 min intervals prior to time 0 following monoclonal antibody (treated) or bovine serum albumin (control) with bolus injection at time 0 followed by infusion of treatments into steers grazing endophyte-infected fescue.

The present invention provides an immunogenic compound comprising the formula:

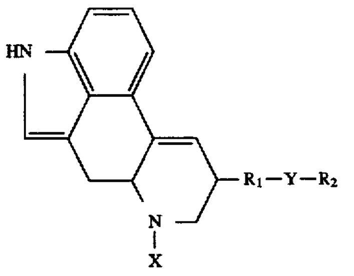

wherein X is selected from the group consisting of methyl and hydrogen;
wherein $R_1$ is a suitable functional group of the lysergic ring;
wherein $R_2$ is an immunogenic protein; and
wherein Y is a bridge to link $R_1$ to $R_2$.

The present invention also provides purified polyclonal and monoclonal antibodies specifically reactive with the immunogenic compound and reactive with the lysergic ring of ergopeptine and clavine alkaloids. The present invention further provides an antibody which is an anti-idiotype of the monoclonal antibody. Also provided are methods of prevention and treatment of fescue toxicosis utilizing the immunogenic compounds and antibodies of the present invention.

DETAILED DESCRIPTION OF THE INVENTION

The present invention may be understood more readily by reference to the following detailed description of specific embodiments and the Examples and Figures included therein.

As used in the claims, "a" means one or more.

The present invention provides an immunogenic compound comprising the formula:

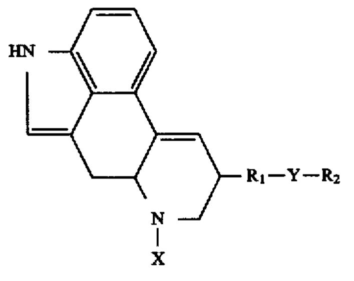

wherein X is selected from the group consisting of methyl and hydrogen;
wherein $R_1$ is a suitable functional group of the lysergic ring;
wherein $R_2$ is an immunogenic protein; and
wherein Y is a bridge to link $R_1$ to $R_2$.

The immunogenic compound embodied by the present invention is synthesized by conjugating a hapten containing the lysergic ring to an immunogenic protein. As it exists in toxins produced by the endophyte *Acremonium coenophialum*, the lysergic ring structure is non-immunogenic. Therefore, it is necessary to conjugate the lysergic ring to an immunogenic protein to produce a compound capable of eliciting a immune response. It can be appreciated by one skilled in the art based on the teachings set forth in the Examples that many variations of the $R_1$, $R_2$, X, and Y groups can be utilized as embodied by the present invention to produce a structure which still carries the core lysergic ring structure as the epitope to stimulate antibody production. The choice of Y as a bridge will ultimately depend upon the choices of $R_1$ and $R_2$.

The core lysergic ring structure is:

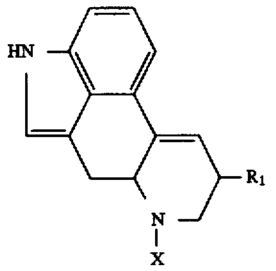

A number of suitable functional groups of the lysergic ring can be utilized at $R_1$ as a starting point for construction of a hapten:

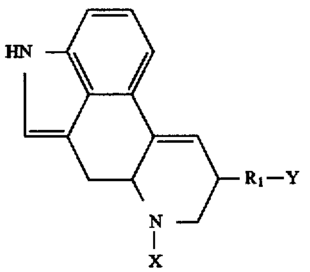

By "suitable functional group of the lysergic ring" is meant to include all groups at the $R_1$ position of the lysergic ring which form natural or synthetically produced derivatives of lysergic acid including, but not limited to alcohol, amine, amide, carboxyl, and hydroxyl. For example, a carboxyl group located at the $R_1$ position of the lysergic ring structure produces lysergic acid, whereas methanol substituted at the $R_1$ position results in lysergol. Lysergamine and lysergamide are functional compounds likewise produced by substitution of amine or amide groups at $R_1$.

In one embodiment of the present invention, the $R_1$ functional group is an alcohol forming lysergol. Compounds which are suitable to effectuate a bridge (Y) to the immunogenic protein $R_2$ include but are not limited to organic acids such as succinic acid, glutaric acid, and dichlorides such as sebacoyl dichloride or trans 1,4-cyclohexandicarboxydichloride.

The alcohol and an anhydride form of the acid can be joined by a mixed anydride reaction as described in the examples. In another embodiment, if an amide group is positioned at $R_1$, then sulfonyl chlorides of organic acids such as succinic sulfonyl chloride can be utilized as bridges to the immunogenic protein. Likewise, acrylic acid can be used to effectuate the bridge when $R_1$ is an amine. Alternatively, acids such as 6-amino-N-hexanoic acid or other suitable amino acids can be utilized to effectuate the bridge when $R_1$ contains a carboxyl group.

Another embodiment of the present invention utilizes ergovaline conjugated to human serum albumin or another suitable immunogenic protein by a dicarbonyl bridge (Y) constructed from a suitable organic acid such as succinic or glutaric acid.

The immunogenic compound of this invention can be synthesized by bridging the lysergic ring to an immunogenic protein, $R_2$, wherein $R_2$ is selected from the group, including but not limited to human serum albumin, bovine serum albumin, chicken globulin, ovalbumin, keyhole limpet hemocyanin, polyarginine, polyhistidine, polytyrosine, polyserine, polyaspartate, and polylysine or combinations of the polyamino acids.

Depending upon the choice of $R_1$ functional groups, one skilled in the art can link $R_2$ utilizing a suitable bridge (Y) by following methods described in Robbins, R. J., "The Measurement of Low-Molecular-Weight, Non-immunogenic Compounds by Immunoassay," In H. F. Linskens and J. F. Jackson (eds.), *Immunology in Plant Sciences*, p. 86–140 (1986).

For example, one embodiment of the present invention provides an immunogenic compound having the formula:

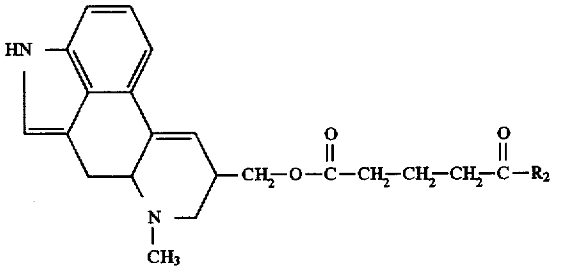

wherein $R_2$ is selected from the group consisting of human serum albumin, bovine serum albumin, chicken globulin, ovalbumin, keyhole limpet hemocyanin, polyarginine, polyhistidine, polytyrosine, polyserine, polyaspartate, and polylysine.

The compounds, once synthesized can be screened to determine immungenicity utilizing the methods set forth in the Examples or by other methods known in the art.

This invention also provides the immunogenic compound described above in a sustained release preparation. This preparation can be utilized as a prophylactic to protect animals from the toxic effects of ergopeptine and clavine alkaloids. Alternatively, the preparation can be used as a therapeutic. As can be appreciated by one skilled in the art, there are many suitable ways to incorporate the immunogenic compound into a sustained release preparation including but not limited to microcapsule and microsphere polymers, liposomes, and polylactic acid preparations. Alternate embodiments of the present invention utilize the immunogenic compounds described above in a biocompatible, biodegradable microsphere polymer or copolymer of polylactide or polyglycolide.

To produce an immunizing agent that will result in prolonged release of the antigen and therefore induce a long term immune response, the antigen can be incorporated, for example, into biodegradable microspheres. The most common agents to make vaccine containing microspheres are polyesters of polylactic add and polyglycolic acid or copolymers of both. The microspheres are produced using mild conditions that do not degrade or damage the antigens. The antigens are trapped in the biodegradable matrix. The three basic methods used to produce these microspheres are as follows:

1. Phase separation—drug and polymer are dispersed or dissolved in a solvent. The microspheres are precipitated out by addition of silicon oil.

2. Solvent extraction—drug and polymer in solution are added to an aqueous solution of poly-(vinyl alcohol) to produce an oil-in-water emulsion. The solvent is then eliminated by adding water and the microspheres dried.
3. Spray drying—drug and polymer are dissolved in a solvent and then sprayed dried.

In all procedures after the spheres are formed, they are dried and then separated into various sizes by sieving.

Factors which affect antigen release are erosion and breakdown of the particles, diffusion of the drug out of the matrix, solubility of the antigen, antigen molecular weight, antigen loading of the spheres and polymer molecular weight. A given antigen release rate is related to particle size; small particles release the antigen sooner than large particles. For prolonged release and immunization a mixture of small and large particles appears to be desirable.

The immunogenic compounds, whether or not contained in a biodegradable microsphere, can be placed in a pharmaceutically acceptable carrier, including but not limited to buffered saline or distilled water. Likewise, the immunogenic compounds can be mixed with a suitable adjuvant, including but not limited to Freund's incomplete adjuvant, saponins or dextrans. Such carriers and adjuvants are well known in the art (Harlow and Lane, *Antibodies: A Laboratory Manual*, Cold Spring Laboratory, Cold Spring Harbor, N.Y. (1988)).

The present invention also provides a method of preventing fescue toxicosis in a herbivore comprising administering a protective mount of the immunogenic compound described above to the herbivore. By "protective amount" is meant an mount sufficient to elicit an immune response to prevent fescue toxicosis in the herbivore. Likewise, a "therapeutic amount" means an amount sufficient to improve the condition of a herbivore having fescue toxicosis. Such an mount can be determined by a skilled artisan given the teachings set forth herein. The immunogenic compound can be used to prevent or treat fescue toxicosis in a herbivore.

The immunogenic compound is capable of stimulating an immune response in all herbivores including but not limited to cattle, horses, sheep, llamas, deer and goats. In one embodiment, the immunogenic compound is administered in an amount ranging from about 1 mg up to about 10mg. This dose will vary based on the weight, type and condition of the animal. This dose can be administered by intramuscular or subcutaneous injection or can be administered as a sustained release implant. In a more preferred embodiment, the protective mount is about 5 mg. It can be appreciated by one skilled in the art that the total protective mount can be divided into a loading dose followed by booster doses at suitable intervals, usually boosters are repeated at two-week intervals.

This invention also provides purified polyclonal and monoclonal antibodies reactive with the lysergic ring of the immunogenic compound, e.g., reactive with the lysergic ring of ergopeptine and clavine alkaloids. These antibodies can be prepared, for example, according to the following examples.

In a presently preferred embodiment of the invention, monoclonal antibodies are produced from the hybridoma cell line designated 15F3.E5. This antibody is specifically reactive with the lysergic ring of the immunogenic compound. The 15F3.E5 antibody was produced from mouse B lymphocytes which formed antibody to a compound of lysergol conjugated to human serum albumin via a glutamic acid bridge. It should be appreciated by one skilled in the art that other monoclonal antibodies designed from the possible combinations for the immunogenic compound as described herein could be utilized to make a purified polyclonal or monoclonal antibody reactive with the lysergic ring. General methods of making various antibodies are descried in Harlow and Lane, *Antibodies: A Laboratory Manual*, Cold Spring Laboratory, Cold Spring Harbor, N.Y. (1988).

The invention also provides a method of protecting a herbivore from fescue toxicosis either therapeutically or prophylactically comprising administering a protective or therapeutic amount of a monoclonal antibody reactive with the immunogenic compound described above to a herbivore. The antibody can be administered intravenously in amounts between about 0.1 mg/kg and 1.3 mg/kg of body weight. In a presently preferred embodiment, the antibody is administered at a dosage of about 0.5 mg/kg of body weight daily.

This invention also provides an antibody which is an anti-idiotype of the monoclonal antibodies of this invention. This invention also provides a method of preventing fescue toxicosis in a herbivore comprising administering a protection inducing amount of the anti-idiotype antibody to the herbivore. The anti-idiotype antibody can be utilized in a vaccine with a suitable adjuvant and/or pharmaceutical carrier as previously described. A preferred embodiment of the invention comprises the anti-idiotype antibody in a sustained released preparation such as a microsphere polymer as discussed above. This preparation can be used as a vaccine to immunize any herbivore including but not limited to cattle, horses, sheep, llamas, deer and goats. As above, the vaccine can be administered, for example, intramuscularly or subcutaneously to the herbivore.

The following considerations are utilized in production of the anti-idiotype antibody. Idiotypic determinants are unique antigenic determinants associated with the antibody binding of antibodies to an antigen. Anti-idiotype antibodies are antibody molecules that react with the idiotypic determinant of a specific antibody (anti-idiotype —$Ab_2$ that reacts with the id of $Ab_1$). Thus, anti-idiotypic antibodies mimic the three dimensional structure of the antigen used to induce $Ab_1$. With these anti-idiotypic antibodies one can induce the production of antibodies ($Ab_3$) which will bind to the same antigen as $Ab_1$.

Anti-idiotype antibodies can be produced by immunizing mice with a monoclonal antibody (all binding sites on all antibody molecules are the same). The spleen cells from this mouse are used to make hybridomas and then the clones produced are selected for the production of anti-idiotype antibodies. The anti-idiotype antibodies are then screened to determine the antibodies which are the mirror image of the antigen, i.e., will block $Ab_1$ from binding to the antigen. These anti-idiotype antibodies can then be used to induce antibody responses to the original antigen (Harlow and Lane, *Antibodies: A Laboratory Manual*, Cold Spring Laboratory, Cold Spring Harbor, N.Y. (1988)).

EXAMPLES

EXAMPLE 1 DEVELOPMENT OF A MONOCLONAL ANTIBODY TO THE LYSERGIC RING COMMON TO THE ERGOT AND CLAVINE ALKALOIDS

Generation of Lysergol and Ergonovine Haptens

Two haptens were generated for ergonovine and lysergol using the mixed anhydride method (Anderson et. al, 1955). Briefly, glutaric and succinic anhydrides were used to make the haptens by placing them with the lysergic derivative and mixing in 1 mL pyridine in 2 mL screw cap vials. Vials were flushed with nitrogen, capped, and placed in the dark for 72 h. Quantities of reagents used to generate each hapten are presented in Table 1.

After the reaction, a stream of $N_2$ was used to evaporate the pyridine, the haptens were resuspended in 2 mL of 0.1M HCl and extracted extensively with ethyl ether. The acidic solutions were neutralized with 0.1M NaOH, frozen and freeze dried. Haptens were resuspended in 1 mL distilled water and loaded onto 20 mL disposable C18 MEGA BOND ELUT® columns (Varian, Harbor City, Calif.; Cat. no. 1225-6023). The columns were washed with 5 mL water and the hapten eluted with 8 mL of 50% aqueous methanol. The hapten solutions were diluted with distilled water to 10% methanol, frozen at −70° C., and freeze dried.

Conjugation of Haptens to Human Serum Albumin

Haptens were conjugated to human serum albumin through the carboxylic residue using the carbodiimide reaction (Robbins, 1986). Thirty-five milligrams of each hapten was added to 40 mg human serum albumin (HSA) in separate 6 ml vials. The hapten and protein was dissolved in 3 mL of 0.03M $KH_2PO_4$ buffer (pH=7.6). The solution was stirred continuously while 1 mL of water containing 20 mg 1-Ethyl-3(Dimethylaminopropyl) carbodiimide hydrochloride (EDC) was added dropwise. Three milligrams of N-hydroxy sulfosuccinimide (NHS) was added and the pH adjusted to 7.6 with 0.1N HCl. The vials were flushed with N, capped and sealed, and stirred continuously for 24 h in the dark at room temperature. Conjugates were dialyzed using 10,000 MW exclusionary tubing in the dark for 24 h at 4° C. The dialyzing solution was 3 L distilled water (pH=7.6) which was changed every 8h. The dialized protein conjugates were frozen at −70° C. and freeze dried.

Hapten/protein ratios of the protein conjugates were determined by diluting the protein conjugate 1:1,000,000 in water and measuring fluorescence of the ergopeptine radical using a Shimadzu (Columbia, MD) HPLC. The HPLC configuration was a Model LC10AS pump equipped with a Model RF535 fluorescence detector. An Alltech (Deerefield, Ill.) ADSORBOSPHERE® HS C18 reverse phase column (cat no. 28930) was used with a mobile phase of 38% acetonitrile with a 0.001M solution of ammonium carbonate per L $H_2O$. Fluorescence of non-conjugated protein was subtracted from that of the protein conjugate and the difference compared to standard dilutions of the respective haptens for quantitation. Conjugate:protein ratios are presented for each hapten in Table 1.

Conjugation of Lysergic Acid to Poly-L-Lysine

For use as an antigen to coat ELISA plates, D-lysergic acid was conjugated to poly-L-lysine hydrobromide (PLL) using the carbidiimide reaction sequence (Robbins, 1986). Twenty-five milligrams of poly-L-lysine hydrobromide and 5 mg lysergic acid were dissolved in 3 mL of 10% aqueous methanol in a 6 mL screwcap vial. The solution was stirred constantly while 1 mL water containing 20 mg EDC was added dropwise. Three milligrams of dry NHS was added and the pH adjusted to 7.6 with 1N HCl. The vial was flushed with nitrogen, capped, and stirred in darkness for 24 h. The PLL conjugate solution was dialyzed exhaustively for 24 h using 10,000 MW exclusionary tubing, frozen at −70° C., and freeze dried overnight. The PLL-lysergic acid conjugate was stored in a desiccator, in the dark, at room temperature.

Mouse Immunization

All mouse handling and cell suspensions, fusions, and cultures were conducted by personnel in the University of Georgia Monoclonal Antibody Facility (Miller Plant Sciences Building, Athens, Ga. 30602). One hundred fifty micrograms of each hapten/HSA conjugate was suspended in 100 uL phosphate buffer solution (PBS) (1.14 g $Na_2HPO_4$, 0.244 g $NaH_2PO_4$, 8.2 g NACl, 1.0 L $H_2O$, pH 7.4) and Freund's complete adjuvant and injected into 3, 4-week old Balb/c mice (Dominion Laboratories, Dublin, Va.) at the base of the tail. Mice were reimmunized 28 d later with a 50 ug hapten/HSA interperitoneal injection using Freund's complete adjuvant. Mouse blood was collected by tail bleeding, the serum diluted 50× with ELISA diluent (10 g bovine serum albumin, 1.17 g $Na_2HPO_4$, 0.244 g $NaH_2PO_4$, 8.2 g NACl, 0.2 g $NaN_3$, 0.5 mL Tween-20, 1 L $H_2O$, pH 7.4) and tested for presence of antibody using ELISA techniques as described below. The mouse with greatest antibody reaction was injected with another 25 ug hapten/HSA suspended in Freund's incomplete adjuvant 14 d after the previous intraperitoneal injection.

Hybridization of B cells and Myelomas

Three days following final hapten/HSA injections, mice were sacrificed by cervical dislocation, their spleens removed, and a suspension of B cells made by macerating the spleen in 40 mL of sterile PBS. The suspension was centrifuged at 300 g for 5 m. Supernatant was poured off and the B cell pellet saved for hybridization with myeloma cells.

Mouse SP2/0 myeloma cells were centrifuged and $10^7$ cells suspended in 10 ml IMDM solution (Sigma Chemical Co., St. Louis, Mo.; cat. no. 17633). Suspended myeloma cells were added to the B cell pellet and centrifuged at 300 g for 5 m. The supernatant was poured off and 0.7 mL of 45% polyethylene glycol was added for 90 s. Fifteen milliliters of IMDM was added and the suspension centrifuged at 300 g for 5 m and supernatant poured off. The cells were resuspended in 90 mL IMDM containing 20% fetal calf serum with HT (FCS/HT) (Sigma Chemical Co., St. Louis, Mo.; cat. no. H0137), and 100 uL of the cell suspensions transferred to 96-well ELISA plates. Cell lines were nourished for 10 days by replenishing the IMDM/FCS/HT medium daily.

Screening Mice and Hybridomas for Antibodies

IMMUNOLN2® 96-well plates (Dynatech Laboratories, Chantilly, Va.) were treated with 50 uL of PBS buffer containing 10 ug PLL-lysergic acid conjugate for 2 h at 21° C. The plates were washed 3×'s using a squirt bottle containing ELISA wash (1.21 g Tris, 0.5 mL Tween 20, 0.2 g $NaN_3$, 1.0 L $H_2O$, pH 8) and blocked with 100 uL bovine serum albumin (BSA) blocking solution (10 g BSA, 0.2 g $NaN_3$, 1.0 L PBS) for 30 m. The plates were washed 3×'s with ELISA wash and 50 uL of diluted mouse serum or hybridoma cell cultures added. After 2 h, the plates were washed 3×'s with ELISA wash and 50 uL of a 1:500 dilution of rabbit anti-mouse antibodies cojugated with alkaline phosphatase (Sigma Chem. Co., St. Louis, Mo.; cat. no. A1902):ELISA diluent added. After 2 h, 50 uL of alkaline phosphatase substrate (0.1 g $MgCl_2$, 96 mL diethanolamine, 1.2 g Disodium p-Nitrophenyl Phosphate, 1 L $H_2O$) was added. The yellow color reaction indicative of presence of mouse antibody binding to PLL-lysergic acid was measured spectrophotometrically at 405 nm using a Titertec Multiskan Model MCC/340 plate reader (Flow Laboratories Inc., McClean, Va.).

One hybridoma cell line, identified as 15F3.E5 tested positive and was expanded to 1.0 L of hybridoma antibody in 12 well culture plates while feeding them with IMDM/HT medium containing 50 mL $L^{-1}$ FCS. Hybridoma solutions from the 24-well culture plates were combined into a common antibody solution to which 0.2 g $NaN_3$ were added to lyse the hybridomas and stabilize the antibody solution.

Determining Cross-reactivity of the Monodonal Antibody

Mouse monoclonal antibody was diluted 1:50 in ELISA diluent. Working dilutions of various lysergic acid derivatives ranging between $1.78\times10^{-6}$ to $3.93\times10^{-15}$M were made in 1:10 increments in PBS and 50 uL aliquots were pre-incubated for 1 h with 50 uL of diluted antibody at room temperature. To determine presence of unbound antibody, pre-incubated antibody/lysergic derivatives were transferred to ELISA plates pre-coated with PLL-lysergic acid for 2 h at room temperature. After washing, ELISA plates were treated with 1:500 dilution of rabbit derived antimouse antibody conjugated to alkaline phosphatase:ELISA diluent for 2 h at room temperature and washed. Fifty microliters of alkaline phosphate substrate was added to each well and the characteristic yellow color indicating binding of mouse antibody to the PLL-lysergic acid measured at 405 nm on a Titertek Multiskan Model MCC/340 plate reader.

EXAMPLE 2 PASSIVE IMMUNIZATION OF MONOCLONAL ANTIBODY 15F3.E5 INTO STEERS SUFFERING FROM FESCUE TOXICOSIS

Preparation of Monoclonal Antibody

Three liters of mouse monoclonal antibody were prepared in 12 well culture plates by feeding the hybridoma 15F3.E5 cell lines with IMDM/HT medium as previously described. The antibody solution was dialyzed against 150 L water over a 24 h period using 12,000 MW exclusionary dialysis tubing to remove excess salts and $NaN_3$. The antibody solution was lyophilized and reconstituted in 300 mL of 0.01M PBS and sterile filtered through a 0.45 micron filter. Protein concentration of the reconstituted antibody solution was 15 mg $mL^{-1}$.

Preparation of Animals Prior to Monoclonal Infusion

Eight yearling Angus steers were randomly assigned to each of two endophyte-infected paddocks 106 days prior to treatment with monoclonal antibody. Endophyte infection rates of the tall fescue plants within the two pastures were 65 and 77.5%. Ergovaline concentration of herbage samples taken immediately prior to monoclonal antibody infusion was 651 and 725 ug $kg^{-1}$, respectively. For a period of four days prior to implementation of the experiment, animals were gentled by tethering them in stalls in a pole barn for 3 to 4 hours where the experiment was to occur.

On Jul. 22, 1992, steers were withheld from water for a 16 h period and weighed. A cannula was placed into each jugular vein for administration of antibody and collection of blood samples. The cannulas were protected by neck wrap and the steers returned to the assigned paddocks.

On July 23, steers were tethered in individual stalls within a pole barn to facilitate administration of the antibody and collection of blood samples. The stalls were arranged parallel to one another with sufficient space for investigators to walk between animals for antibody treatment and sample collection. Steers remained in the stalls for approximately eight hours during the experiment. Bermudagrass hay and water was provided during animal confinement.

Infusion of Monoclonal Antibody

The four steers within each tall fescue paddock were ranked by the 16 h off water weights. Steers were assigned to groups of two based upon rank, and two treatments (control and antibody) were randomly assigned within the groups of two. The antibody treatment group averaged 297 kg (S.D.=19.7) and the control treatment group averaged 304 kg (S.D.=11.6). The control treatment group received a bovine serum albumin placebo at the same rate as the group which received the monoclonal antibody 15F3.E5. Prior to administration of treatments, three sham blood samples were collected at 30 min intervals to accustom the animals to blood collection. Three more samples were taken from which basal circulating prolactin could be determined.

Immediately after the final basal blood sample was collected, the steers were given IV bolus injections of 0.62 mg $kg^{-1}$ of reconstituted monoclonal antibody or bovine serum albumin in sterile phosphate buffer solution (SPBS) (8.5 g NaCl, 2.18 g $Na_2(HPO_4)7H_2O$, 0.32 g $Na(H_2PO_4)$ $H_2O$, pH=7.1). The antibody and BSA treatments were diluted in SPBS to 3 mg protein $mL^{-1}$ and infused IV at a rate of 30 mg $steer^{-1}$ $h^{-1}$ for a 5 h period. Infusions were administered using Ismatec-SA Model 7613-30 programmable pumps (Basel, Switzerland). Antibody dosage was based upon a report of circulating ergovaline at a concentration of 40 ng $L^{-1}$ (Savary et al., 1990). Antibody dosage was derived as being approximately 1000×'s the concentration of circulating ergovaline.

Blood was collected at 30 min intervals after initial administration of the treatments. At the end of the infusion period, all steers were given 33 ug $kg^{-1}$ thyrotropin releasing hormone (TRH) IV as a test challenge for prolactin secretion. Blood was collected at 10 and 20 min intervals after TRH treatment. All blood samples were permitted to clot at ambient temperature, stored on ice in the field, and then at −4° C. overnight. Serum was harvested following centrifugation and stored at −20° C. for prolactin determination.

Measurement of Prolactin and Prolactin Response

The concentration of prolactin in the serum was determined by radioimmune assay procedures adapted from Wallner et al., (1983) and used by Thompson et al., (1992). Reagents used were USDA-b-Prl-B-1-s bovine prolactin as a standard, iodinated USDA-b-Prl-I-s bovine prolactin ($I^{125}$) and DJB-7-0330 rabbit anti-bovine prolactin antisera for binding. The prolactin-bound rabbit anti-sera was precipitated using 6% polyethylene glycol with guinea pig anti-rabbit antisera. All prolactin measurements were made in a single assay. Two control serum pools (high and low) were included for quality control (n=6). Means and coefficients of variation for each were 14.17 ng $mL^{-1}$ and 6.5%, and 7.74 ng $mL^{-1}$ and 10.4%, respectively, which were considered acceptable. Data were analyzed by analysis of variance using a split-plot model with antibody treatment as the main effect and time after initial administration as the split. A significant time×treatment interaction occurred. Therefore, linear and quadratic coefficients were determined using regression analysis to relate percent and absolute changes from basal values over time.

EXAMPLE 3 ACTIVE IMMUNIZATION OF ANGUS HEIFERS AGAINST FESCUE TOXICOSIS

Nine yearling Angus heifers were maintained on cereal rye (*Secale cereale* L.) pastures from mid-December, 1991 through May, 1992. The heifers received 2.7 kg $head^{-1}$ $day^{-1}$ of a concentrate diet at the onset of grazing through March, 1992. Heifers were randomly assigned to three treatment groups which were immunized with either the ergonovine-glutaric, lysergol-glutaric, or lysergol-succinic haptens conjugated to HSA (Table 1).

TABLE 1

Quantities of reagents used to generate haptens for conjugation to immunizing proteins and their molar ratios of the protein conjugates.

| Hapten/Protein Alkaloid Derivative Ratio | mg | Anhydride | mg | Molar |
|---|---|---|---|---|
| Ergonivine | 55 | Glutaric | 67 | 8.52 |
| Ergonovine | 20 | Succinic | 13 | 3.15 |

TABLE 1-continued

Quantities of reagents used to generate haptens for conjugation to immunizing proteins and their molar ratios of the protein conjugates.

| Hapten/Protein Alkaloid Derivative Ratio | mg | Anhydride | mg | Molar |
|---|---|---|---|---|
| Lysergol | 40 | Glutaric | 49 | 12.20 |
| Lysergol | 40 | Succinic | 13 | 8.50 |

The first injection was given on Jan. 16, 1992 using 1.0 mg of immunogen dissolved in 1.0 mL SPBS plus 1.0 mL of Freund's complete adjuvant IM in the neck region. Subsequent injections using 0.5 mg of immunogen were given on January 30 and February 14. Animals were maintained in a single group after each injection. Serum titer for antibody was conducted by the ELISA technique outlined in the methods for the monoclonal antibody. Blood was collected prior to initial immunization and at 2 week intervals through Mar. 26, 1992 and again on May 18, 1992.

RESULTS

EXAMPLE 1 DEVELOPMENT OF A MONOCLONAL ANTIBODY TO THE LYSERGIC RING COMMON TO THE ERGOPEPTINE AND CLAVINE ALKALOIDS

A mouse immunized with lysergol linked to HSA via glutaric anhydride gave the greatest immune response. Only 29 hybridoma lines were viable, one of which had affinity to PLL-LYS as indicated by ELISA. The cell line, 15F3.E5, expressed cross reaction to lysergol, lysergic acid, ergovaline, ergonovine, and ergotamine tartrate, suggesting that the antibody recognized the lysergic ring structure common to the ergopeptine and clavine alkaloids (Table 2).

TABLE 2

Molar concentration of lysergic acid derivatives needed to give 50% maximum absorbance when analyzed in a competitive ELISA assay.

| Lysergic Acid Derivative | Molar Concentration at 50% Maximum Absorbance |
|---|---|
| Lysergol | $3.93 \times 10^{-15}$ |
| Lysergic Acid | $3.73 \times 10^{-11}$ |
| Ergovaline | $1.00 \times 10^{-11}$ |
| Ergonovine | $1.69 \times 10^{-9}$ |
| Ergotamine tartrate | $7.69 \times 10^{-9}$ |
| 2-bromo-a-ergocryptine | $>1.33 \times 10^{-6}$ |
| dihydro-ergocornine | $>1.68 \times 10^{-6}$ |
| dihydro-ergocristine | $>1.78 \times 10^{-6}$ |

Hydrogenation or bromation of the ring structure resulted in no cross reaction with those compounds at the concentration at which they were tested. It is likely that hydrogenation or bromation resulted in conformational changes of the lysergic ring structure. Therefore, the monoclonal antibody 15F3.E5 was highly specific to the intact lysergic ring.

EXAMPLE 2 PASSIVE IMMUNIZATION OF MONOCLONAL ANTIBODY 15F3.E5 INTO STEERS SUFFERING FROM FESCUE TOXICOSIS

Figure 1B:
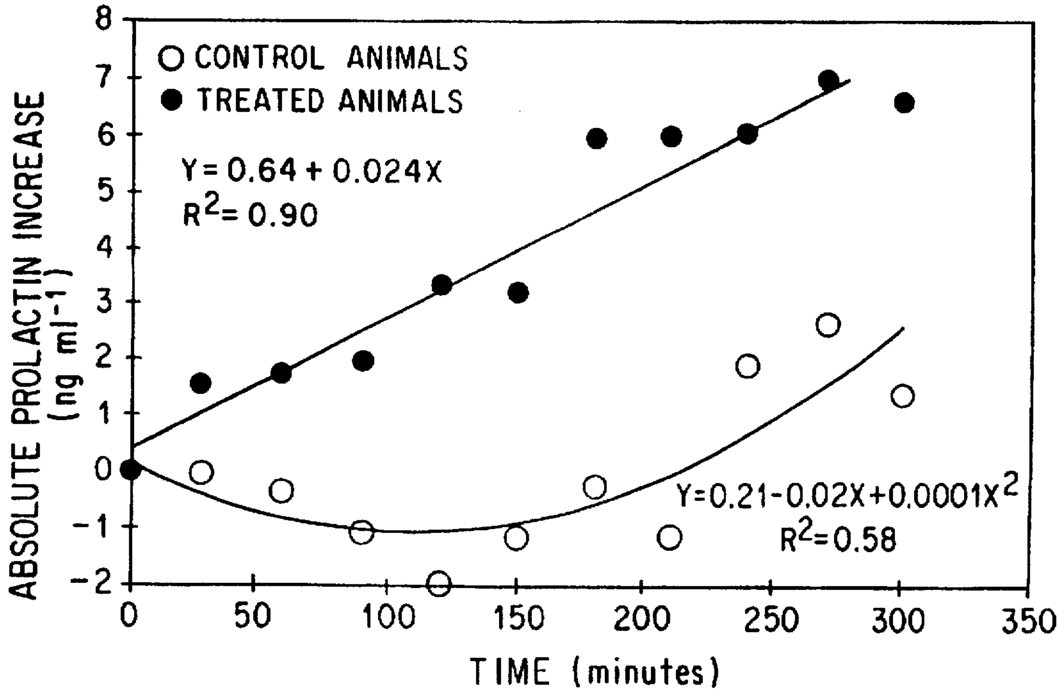
FIG 1*b* depicts absolute serum prolactin changes from three basal values collected at 30 min intervals prior to time 0 following monoclonal antibody (treated) or bovine serum albumin (control) with bolus injection at time 0 followed by infusion of treatments into steers grazing endophyte-infected fescue.

Mean serum PRL prior to bolus treatment was 23.8 and 18.8 ng $mL^{<1}$ in control and treated steers respectively. Because circulating PRL was variable among steers, the data was analyzed as percentage and absolute change from the basal measurements for each animal. The regression equation describing increased percent serum PRL in response to monoclonal antibody infusion had an intercept not different from 0.0 (p=0.70), and positive linear and negative quadratic coefficients (p=0.02). This suggests that the rate of percent increase in serum prolactin decreased as time progressed (FIG. 1*a*). Conversely, control animals had a negative linear coefficient and positive quadratic coefficient (p=0.02). The regression equation describing absolute increased serum PRL in animals receiving antibody was linear with a positive coefficient (p=0.01) and an intercept not different from 0.0 (p=0.25) (FIG. 1*b*). Control animals had negative linear and positive quadratic coefficients. All animals responded to TRH (97.1–100% increase in control and treated steers, respectively).

It is important to note that an increases in serum PRL was immediate among the steers receiving the monoclonal antibody. While absolute serum PRL increased at a linear rate, the rate of percent change in PRL decreased in steers receiving antibody as time progressed. Serum PRL increased in control steers receiving BSA, but after 150 min only. We attribute the increase serum PRL in the control steers to anxiety among animals from their confinement.

These results demonstrate that the monoclonal antibody, specific for the lysergic ring of the ergopeptine and clavine alkaloids, reversed a sign of fescue toxicosis. Since the antibody binds ergopeptine alkaloids, specifically ergovaline, and the antibody neutralized circulating ergopeptine alkaloids, this resulted in increased PRL. This is the first definitive evidence that the ergopeptine alkaloids are directly involved in animal responses to endophyte-infected tall fescue.

EXAMPLE 3 ACTIVE IMMUNIZATION OF ANGUS HEIFERS AGAINST FESCUE TOXICOSIS

Figure 2:
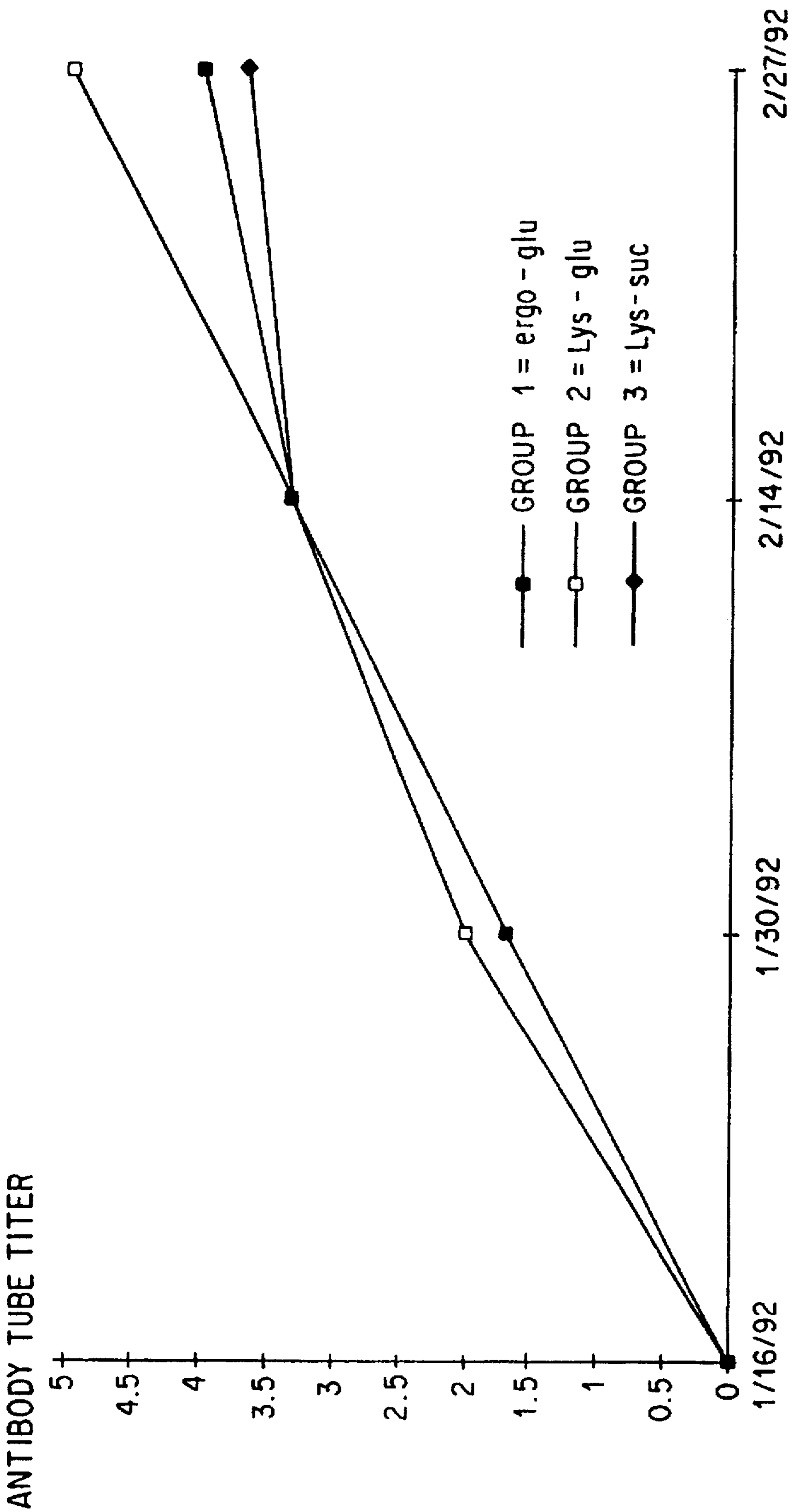
FIG. 2 depicts an antibody response of Angus heifers immunized on three separate days with lysergic acid derivatives conjugated to human serum albumin. Average antibody titers for Group I and Group III between Jan. 16, 1992 and Feb. 14, 1992 are not shown separately, because the average titers for Groups I and III were the same during the time period between Jan. 16, 1992 and Feb. 14, 1992.

Antibodies to the lysergic ring were stimulated in all animals regardless of the immunogen used (FIG. 2). Titer increased linearly with subsequent injections and continued until 2 weeks after final immunization. Tilers demonstrate that animal responses to the immunogens were not different from one another.

It should be noted that the ELISA procedure used to determine antibody production uses lysergic acid as the hapten. Therefore, antibodies recognizing the lysergic acid hapten are likely to have broad spectrum activity on other compounds with the lysergic ring. Therefore, antibodies generated by active immunization have activity similar to that of the mouse monoclonal antibody and provide protection to the clavine and ergopeptine alkaloids.

Throughout this application, various publications are referenced. The disclosures of these publications in their entireties are hereby incorporated by reference into this application in order to more fully describe the state of the art to which this invention pertains.

REFERENCES

1. Aguado, M. T., Lambert, P. H., "Controlled-Release Vaccines-Biodegradable Polylactide/Polyglycolide (PL/PG) Microspheres as Antigen Vehicles," *Immunobiol.,* 184:113–125 (1992).
2. Anderson, G. W., Zimmerman, J. E. and F. M. Callahan, "The use of esters of N-hydroxysuccinimide in peptide synthesis," *J. Am. Chem. Soc.* 85:1839 (1963).
3. Bacon, C. W., Siegel, M. R., "Endophyte Parasitism of Tall Fescue," *J. Prod. Agric.,* 1(1):45–55 (1988).
4. Bond, J., J. B. Powell, D. J. Undersander, P. W. Moe, H. F. Tyrrell, and R. R. Oltjen, "Forage Composition and Growth and Physiological Characteristics of Cattle Grazing Several Varieties of Tall Fescue During Summer Conditions," *J. Anim. Sci.* 59:584–[?] (1984).
5. Bruce, L. A., Robbins, J. D., and Huber, T. L., "Smooth muscle response to fescue alkaloids," *J. Anim. Sci.* 32:373, Abstr. No. 18, (1971).
6. Burns, J. C. and Chamblee, D. S., Adaptation, p. 9–30. In R. C. Buckner and L. P. Bush (ed.) Tall Fescue. *Special Publication No.* 20, American Society of Agronomy, Madison, Wis. (1979).
7. Bush, L. P., Boling J. and Yates, S., "Animal disorders," p. 247–292. In R. C. Buckner and L. P. Bush (ed.) Tall Fescue. *Special Publication No.* 20, American Society of Agronomy, Madison, Wis. (1979).
8. Chanh, T. C., Siwak, E. B., Hewetson, J. F., "Contemporary Issues in Toxicology Anti-idiotype-Based Vaccines against Biological Toxins," *Toxicology and Applied Pharmacology,* 108:183–193 (1991).
9. Dougherty, C. T., Lauriault, L. M., Bradley, N. W., Gay, N., Cornelius, P. L., "Induction of Tall Fescue Toxicosis in Heat-Stressed Cattle and its Alleviation with Thiamin[1, 2], *J. Anim. Sci.,* 69:1008–1018 (1991).
10. Garner, G. B. and Cornell, C. R., "Fescue Foot in Cattle," p. 45–62. In T. D. Wyllie and M. G. Morehouse (eds.) Mycotoxic fungi, mycotoxins, and mycotoxicoses, Marcel Dekker, New York, (1978).
11. Harlow and Lane, *Antibodies: A Laboratory Manual,* Cold Spring Laboratory, Cold Spring Harbor, N.Y. (1988).
12. Hill, N. S. and Stringer, W. C., "Surveying for the Fungat Endophyte, *Acremonium coenophialum,* in Tall Fescue Pastures of South Carolina, *Agron. Abs.* 77:18 (1985).
13. Kellerman, T. S., Coetzer, J. A. W. and Naude, T. W., "Heart," p. 83, In T. S. Kellerman and J. A. W. Coetzer (eds.) Plant poisoning and mycotoxicoses of livestock in Southern Africa. Oxford Univ. Press, Cape Town (1988).
14. Kohler, G. and Milstein, C., "Continuous Cultures of Fused Cells Secreting Antibody of Predefined Specificity," *Nature,* 256:495–497 (1975).
15. Lechat, P., Mudgett-Hunter, M., Margolies, M. N., Haber, E. and Smith, T. W., "Reversal of Lethal Digoxin Toxicity in Guinea Pigs Using Monoclonal Antibodies and Fab Fragments," *J. Pharmac. Exp. Ther.* 229:210 (1984).
16. Lipham, L. B., Thompson, F. N., Stuedemann, J. A. and Sartin, J. L., "Effects of Metoclopramide on Steers Grazing Endophyte-Infected Fescue," *J. Anim. Sci.* 67:1090–[?] (1989).
17. Mattocks, A. R., "Toxicity of Pyrrolizidine Alkaloids, *Nature* 217:723–728 (1968).
18. Mizinga, K. M., "The Effect of Feeding Endophyte-Infected Fescue Seed on Luteinizing Hormone Secretion in Cows and Neural Dopamine Receptors in Rats," *Ph.D. Dissertation,* University of Georgia, Athens, Ga. (1991).
19. Putnam, M. R., Bransby, D. I., Schumacher, J.,Boosinger, T. R., Bush, L., Shelby, R. A., Vaughan, J. T., Ball, D., Brendemuehl, J. P., "Effects of the Fungal Endophyte *Acremonium coenophialum* in Fescue on Pregnant Mares and Foal Viability," *Am. J. Vet. Res.,* 52(12):2071–2074 (December 1991).
20. Robbins, R. J. 1986. "The Measurement of Low-Molecular-Weight, Non-Immunogenic Compounds by Immunoassay," p.86–140. In H. F. Linskens and J. F. Jackson (eds.) *Immunology in Plant Sciences,* Springer-Verlag, New York (1986).

21. Savary, B. J., Gwinn, K. D., Oliver, J. W., Chestnut, A. B., Linnabary, R. D., Mclaren, J. B. and Fribourg, H. A., "Analysis of Ergopeptine Alkaloids in Bovine Iserum," *Int. Symposium on Acremonium/Grass Interactions* 263. (Abstr.). Louisiana State University, New Orleans, La. (1990).

22. Shelby, R. A., and Dalrymple, L. W., "Incidence and Distribution of the Tall Fescue Endophyte in the United States," *Plant Disease* 71:783–786 (1987).

23. Siegel, M. R., Latch, G. C. M., Bush, L. P., Fannin, N. F., Rowen, D. D., Tapper, B. A., Bacon, C. W., and Johnson, M. C., "Alkaloids and Insecticidal Activity of Grasses Infected With Fungal Endophytes," *J. Chem. Ecol.* 16:3301–3315 (1991).

24. Solomons, R. N., Oliver, J. W. and Linnabary, R. D., "Reactivity of Dorsal Pedal Vein of Cattle to Selected Alkaloids Associated with *Acremonium coenophialum*-infected Fescue Grass, *Am. J. Vet. Res.*, 50:235–238 (1989).

25. Stuedemann, J. A., Rumsey, T. S., Bond, J., Wilkinson, S. R., Bush, L. P., Williams, D. J. and Caudle, A. B., "Association of Blood Cholesterol with Occurrence of Fat Necrosis in Cows and Tall Fescue Summer Toxicosis in Steers," *Am. J. Vet. Res.*, 46:1990–1995 (1985).

26. Testereci, H., Garner, G. B., Cornell, C. N., "Fescue Toxicosis: Cattle Response to IV Infusion of an Ergovaline Enriched Fraction in a Climate Controlled Chamber," In *Proc. Amer. Foliage and Grassland Conference*, Columbia, Mo. (Apr. 1–4, 1991).

27. Yates, S. G., Grove, M. D., and Tookey, H. L., "Assay of Toxic Forage," p. 108–113. In *Proc. Fescue Toxicity Conf.*, Lexington, Ky., 31 May-1 June, University of Missouri, Columbia, Mo. (1973).

What is claimed is:

1. A method of preventing fescue toxicosis in a herbivore comprising administering a therapeutic amount of an immunogenic compound having the formula:

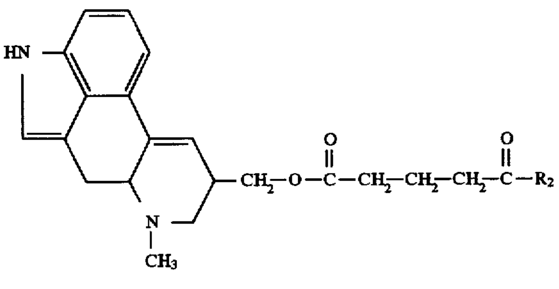

wherein $R_2$ is selected from the group consisting of human serum albumin, bovine serum albumin, chicken globulin, ovalbumin, keyhole limpet hemocyanin, polyarginine, polyhistidine, polytyrosine, polyserine, polyaspartate, and polylysine.

2. A method of treating fescue toxicosis in a herbivore comprising administering a therapeutic amount of an immunogenic compound having the formula:

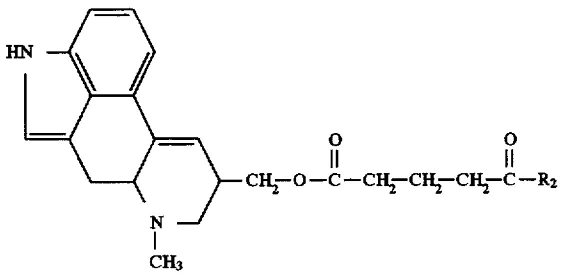

wherein $R_2$ is selected from the group consisting of human serum albumin, bovine serum albumin, chicken globulin, ovalbumin, keyhole limpet hemocyanin, polyarginine, polyhistidine, polytyrosine, polyserine, polyaspartate, and polylysine.

3. A method of preventing fescue toxicosis in a herbivore comprising administering to the herbivore a fescue toxicosis protective amount of an immunogenic compound of an alkaloid-protein conjugate having the formula:

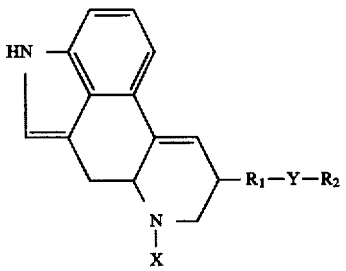

wherein the alkaloid of the alkaloid-protein conjugate consists of the lysergic ring including X and $R_1$;

wherein X is selected from the group consisting of methyl and hydrogen;

wherein $R_1$ linked to the lysergic ring but prior to being linked to Y is —$CO_2H$, —$CH_2OH$, —OH, —$NH_2$ or —C(O)$NH_2$;

wherein $R_2$ is an immunogenic protein; and wherein Y is a bridge to link the alkaloid at $R_1$ to the protein $R_2$.

4. The method of claim 3, wherein $R_1$ linked to the lysergic ring but prior to being linked to Y is —$CO_2H$.

5. The method of claim 3, wherein $R_1$ linked to the lysergic ring but prior to being linked to Y is —$CH_2OH$.

6. The method of claim 3, wherein $R_1$ linked to the lysergic ring but prior to being linked to Y is —OH.

7. The method of claim 3, wherein $R_1$ linked to the lysergic ring but prior to being linked to Y is —$NH_2$.

8. The method of claim 3, wherein $R_1$ linked to the lysergic ring but prior to being linked to Y is —C(O)$NH_2$.

9. The method of claim 3, wherein the lower limit of the protective amount is 5 mg.

10. A method of treating fescue toxicosis in a herbivore comprising administering to the herbivore a therapeutic amount of an immunogenic compound of an alkaloid-protein conjugate having the formula:

wherein the alkaloid of the alkaloid-protein conjugate consists of the lysergic ring including X and $R_1$;

wherein X is selected from the group consisting of methyl and hydrogen;

wherein $R_1$ linked to the lysergic ring but prior to being linked to Y is —$CO_2H$, —$CH_2OH$, —OH, —$NH_2$ or —C(O)$NH_2$;

wherein $R_2$ is an immunogenic protein; and wherein Y is a bridge to link the alkaloid at $R_1$ to the protein $R_2$.

11. The method of claim 10, wherein $R_1$ linked to the lysergic ring but prior to being linked to Y is —$CO_2H$.

12. The method of claim 10, wherein $R_1$ linked to the lysergic ring but prior to being linked to Y is —$CH_2OH$.

13. The method of claim 10, wherein $R_1$ linked to the lysergic ring but prior to being linked to Y is —OH.

14. The method of claim 10, wherein $R_1$ linked to the lysergic ring but prior to being linked to Y is —$NH_2$.

15. The method of claim 10, wherein $R_1$ linked to the lysergic ring but prior to being linked to Y is —$C(O)NH_2$.

16. The method of claim 10, wherein the lower limit of the therapeutic amount is 5 mg.

17. The method of claim 9, wherein the herbivore is a horse or a cow.

18. The method of claim 16, wherein the herbivore is a horse or a cow.

* * * * *

UNITED STATES PATENT AND TRADEMARK OFFICE

CERTIFICATE OF CORRECTION

PATENT NO. : 5,718,900
DATED : February 17, 1998
INVENTOR(S) : Hill et al.

It is certified that error appears in the above-identified patent and that said Letters Patent is hereby corrected as shown below:

Title page,
Add as an assignee, -- The United States of America, as represented by the Secretary of Agriculture --.

Signed and Sealed this

Thirtieth Day of October, 2001

*Attest:*

Nicholas P. Godici

NICHOLAS P. GODICI

*Attesting Officer* *Acting Director of the United States Patent and Trademark Office*